(12) United States Patent
Wiggins et al.

(10) Patent No.: US 10,478,129 B2
(45) Date of Patent: Nov. 19, 2019

(54) METHODS FOR IMPROVING RESPONSE TIME, ROBUSTNESS AND USER COMFORT IN CONTINUOUS ESTIMATION OF BIOPHYSIOLOGICAL RATES

(71) Applicant: Samsung Electronics Co., LTD, Gyeonggi-DO (KR)

(72) Inventors: Matthew C. Wiggins, San Jose, CA (US); Asif Khalak, Belmont, CA (US); Yelei Li, Santa Clara, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 511 days.

(21) Appl. No.: 14/931,440

(22) Filed: Nov. 3, 2015

(65) Prior Publication Data

US 2016/0220192 A1    Aug. 4, 2016

Related U.S. Application Data

(60) Provisional application No. 62/110,263, filed on Jan. 30, 2015, provisional application No. 62/112,032, filed on Feb. 4, 2015, provisional application No. 62/113,092, filed on Feb. 6, 2015.

(51) Int. Cl.
*A61B 5/00* (2006.01)
*A61B 5/024* (2006.01)
*A61B 5/0402* (2006.01)
*A61B 5/08* (2006.01)
(Continued)

(52) U.S. Cl.
CPC ........ *A61B 5/7264* (2013.01); *A61B 5/02416* (2013.01); *A61B 5/0402* (2013.01); *A61B 5/0816* (2013.01); *A61B 5/1455* (2013.01); *A61B 5/7203* (2013.01); *A61B 5/7207* (2013.01); *A61B 5/7221* (2013.01); *A61B 5/7225* (2013.01); *A61B 5/7253* (2013.01); *A61B 5/7278* (2013.01); *G01N 33/4833* (2013.01)

(58) Field of Classification Search
CPC .......... G01N 33/4833; A61B 5/7264; A61B 5/7225; A61B 5/7203; A61B 5/1455; A61B 5/0816; A61B 5/7221; A61B 5/7207; A61B 5/0402; A61B 5/7253; A61B 5/7278; A61B 5/02416
See application file for complete search history.

(56) References Cited

U.S. PATENT DOCUMENTS

| 8,858,450 | B2 * | 10/2014 | Chon | A61B 5/0806 600/484 |
| 2007/0219453 | A1 * | 9/2007 | Kremliovsky | A61B 5/0452 600/509 |
| 2009/0105556 | A1 * | 4/2009 | Fricke | A61B 5/0059 600/301 |

* cited by examiner

Primary Examiner — Mark Bockelman (57) ABSTRACT

A computer-implemented method for estimating biophysiological rates using the Hilbert transform includes receiving a quasiperiodic data stream from a biophysiological sensor, and removing at least a portion of an offset from the quasiperiodic data stream to provide a smoothed data stream by filtering the quasiperiodic data stream through a bandpass filter and phase compensating the filtered quasiperiodic data stream. The method also includes transforming the smoothed data stream into an analytic data stream using a Hilbert transform approximation and calculating the time derivative of the phase angle of the analytic data stream, where the time derivative is a frequency of the quasiperiodic data stream. The method further includes providing an output data stream derived from the frequency.

19 Claims, 5 Drawing Sheets

(51) Int. Cl.
*A61B 5/1455* (2006.01)
*G01N 33/483* (2006.01)

METHODS FOR IMPROVING RESPONSE TIME, ROBUSTNESS AND USER COMFORT IN CONTINUOUS ESTIMATION OF BIOPHYSIOLOGICAL RATES

CROSS-REFERENCE TO RELATED APPLICATIONS

This application claims the benefit of U.S. Provisional Application No. 62/110,263, filed Jan. 30, 2015; U.S. Provisional Application No. 62/112,032, filed Feb. 4, 2015; and U.S. Provisional Application No. 62/113,092, filed Feb. 6, 2015, which are incorporated by reference herein.

TECHNICAL FIELD

This description relates generally to signal processing, and more particularly to a method for improving response time, robustness, and user comfort in continuous estimation of biophysiological rates.

BACKGROUND

Signal processing generally encompasses collecting, organizing, transforming and summarizing raw input data to produce meaningful or useful information, or output data. Signal processing is the enabling technology for the generation, transformation, and interpretation of information. Signal processing typically uses computational or heuristic representations and techniques to acquire, extract, represent, model or analyze data embedded in an analog or digital signals, including, for example, audio, image, video, controls, radio frequency, and other electrical signals.

In general, signal processing entails processes such as sampling sensor and instrument signals; analog-to-digital (A/D or ADC) and digital-to-analog (D/A or DAC) conversion of signals; filtering signals for the purpose of noise reduction, enhancement, reconstruction of the original signal or an approximation of the signal, and the like. Computational techniques and mathematical models employed include, for example, arithmetic operations, differential and integral calculus, differential equations, transform theory, time-frequency analysis of non-stationary signals, spectral analysis, probability and statistical analysis, vector analysis and linear algebra, parametric signal modeling, detection theory, estimation theory, optimization, and other numerical methods.

Digital signal processing (DSP) typically is carried out by general purpose computers or specialized controllers. DSP makes use of discrete mathematics, including the representation of discrete time series, discrete frequency, and other discrete domain signals as a sequence of numbers or symbols and the processing of these signals. Discrete-time signal processing generally applies to sampled signals, such as signals generated by electrical, optical, or electromechanical sensors.

Nonlinear signal processing involves the analysis and processing of signals produced from nonlinear systems in the time, frequency, or spatio-temporal domains. Nonlinear systems produce relatively complex signal characteristics that in some cases cannot be modeled or analyzed using linear methods.

The Hilbert transform is a linear operator that shifts the phase of frequency components of a function or signal in the same domain as the original function or signal. Complex, sequential, discrete pairs, [u(t), û(t)] or [u(t), Hu(t)], in which the real part is represented by the original function or signal and the imaginary part is represented by the discrete Hilbert transform of the function or signal compose an analytical signal. The Hilbert transformed series has the same amplitude and frequency content as the original function or signal, and includes phase information that correlates to the phase of the original function or signal.

In general, the Hilbert transform is useful in calculating instantaneous attributes of a time series, in particular, amplitude and frequency. The amplitude of the analytical signal is equal to the instantaneous amplitude of the original signal, and the time rate of change of the phase angle of the analytical signal is equal to the instantaneous frequency of the original signal.

Cardiovascular periodicity generally refers to the nearly regular, recurrent blood pressure and volume pulses induced by the heart. The time length of each period between consecutive individual heart beats is commonly referred to as the interbeat interval (IBI, or RR interval). The heart rate is the inverse of the cardiovascular periodicity.

During normal heart functioning, there is some variation in the continuous time series of IBI values. This natural variation is known as heart rate variability (HRV). Relatively noisy or low-amplitude sensor signals can add measurement error that further detracts from the nearly periodic nature of the observed heart beat signal. Thus, the observed heart beat sensor signal typically represents a quasiperiodic function. That is, the signal is similar to a periodic function, but displays irregular periodicity and does not meet the strict definition of a periodic function that recurs at regular intervals. Quasiperiodic behavior includes a pattern of recurrence with a component of unpredictability that does not lend itself to precise measurement.

The time intervals between consecutive heart beats are customarily measured in an electrocardiogram (ECG or EKG) from the initiation of each of two consecutive QRS complexes, corresponding to the contraction of the heart ventricles, each of which typically includes three component waveforms (the Q-wave, R-wave and S-wave). However, the initiation of the QRS complex can be difficult to locate in relatively noisy or low-amplitude sensor signals, which can lead to measurement error. Thus, IBI sometimes is measured between R-wave peaks in consecutive heart beats to reduce measurement error.

IBI can also be determined from a peripheral pulse measurement, such as a digital volume pulse measurement, such as a photoplethysmogram (PPG), an optically obtained plethysmogram, or volumetric measurement of an organ. The pulse oximeter, a known type of PPG sensor, illuminates the skin with one or more colors of light and measures changes in light absorption at each wavelength. The PPG sensor illuminates the skin, for example, using an optical emitter, such as a light-emitting diode (LED), and measures either the amount of light transmitted through a relatively thin body segment, such as a finger or earlobe, or the amount of light reflected from the skin, for example, using a photodetector, such as a photodiode. PPG sensors have been used to monitor respiration and heart rates, blood oxygen saturation, hypovolemia, and other circulatory conditions.

Conventional PPGs typically monitor the perfusion of blood to the dermis and subcutaneous tissue of the skin, which can be used to detect, for example, the change in volume corresponding to the pressure pulses of consecutive cardiac cycles of the heart. If the PPG is attached without compressing the skin, a secondary pressure peak can also be seen from the venous plexus. A microcontroller typically processes and calculates the primary peaks in the waveform signal to count heart beats per minute (bpm).

Offsets, or DC shifts, can occur in biophysiological sensor signals as a result of inconsistencies in the interface between a subject and a sensor, such as an ECG electrode or a PPG optical sensor. The subject may include, but not limited to, a person, an animal, and a living organism. As a result, sensor designs typically must ensure a reliable mechanical interface between the subject and the sensor. In the case of some wearable devices with biophysiological sensors, including, for example, wrist-based wearables, there is a direct relationship between comfort (corresponding to a relatively loose attachment) and a reliable mechanical interface (corresponding to a relatively tight attachment).

SUMMARY

According to one embodiment, an apparatus for estimating biophysiological rates using a Hilbert transform includes a memory that stores machine instructions and a processor coupled to the memory that executes the machine instructions to receive a quasiperiodic data stream from a biophysiological sensor, remove at least a portion of an offset from the quasiperiodic data stream to provide a smoothed data stream by filtering the quasiperiodic data stream through a bandpass filter and phase compensating the filtered quasiperiodic data stream, transform the smoothed data stream into an analytic data stream using a Hilbert transform approximation, calculate a time derivative associated with a phase angle of the analytic data stream, and provide an output data stream derived from a frequency, wherein the frequency is the time derivative of the quasiperiodic data stream.

According to another embodiment, a method for estimating biophysiological rates using the Hilbert transform includes receiving a quasiperiodic data stream from a biophysiological sensor, and removing at least a portion of an offset from the quasiperiodic data stream to provide a smoothed data stream by filtering the quasiperiodic data stream through a bandpass filter and phase compensating the filtered quasiperiodic data stream. The method also includes transforming the smoothed data stream into an analytic data stream using a Hilbert transform approximation, and calculating the time derivative associated with the phase angle of the analytic data stream, where the time derivative is a frequency of the quasiperiodic data stream. The method further includes providing an output data stream derived from the frequency.

According to yet another embodiment, a computer program product for estimating biophysiological rates using a Hilbert transform includes a non-transitory, computer-readable storage medium encoded with instructions adapted to be executed by a processor to implement receiving a quasiperiodic data stream from a biophysiological sensor, and removing at least a portion of an offset from the quasiperiodic data stream to provide a smoothed data stream by filtering the quasiperiodic data stream through a bandpass filter and phase compensating the filtered quasiperiodic data stream. The instructions are further adapted to implement transforming the smoothed data stream into an analytic data stream using a Hilbert transform approximation, calculating a time derivative associated with a phase angle of the analytic data stream, where the time derivative is a frequency of the quasiperiodic data stream, and providing an output data stream derived from the frequency.

The details of one or more embodiments of the present disclosure are set forth in the accompanying drawings and the description below. Other features, objects, and advantages of the present disclosure will be apparent from the description and drawings, and from the claims.

DETAILED DESCRIPTION

Figure 1:
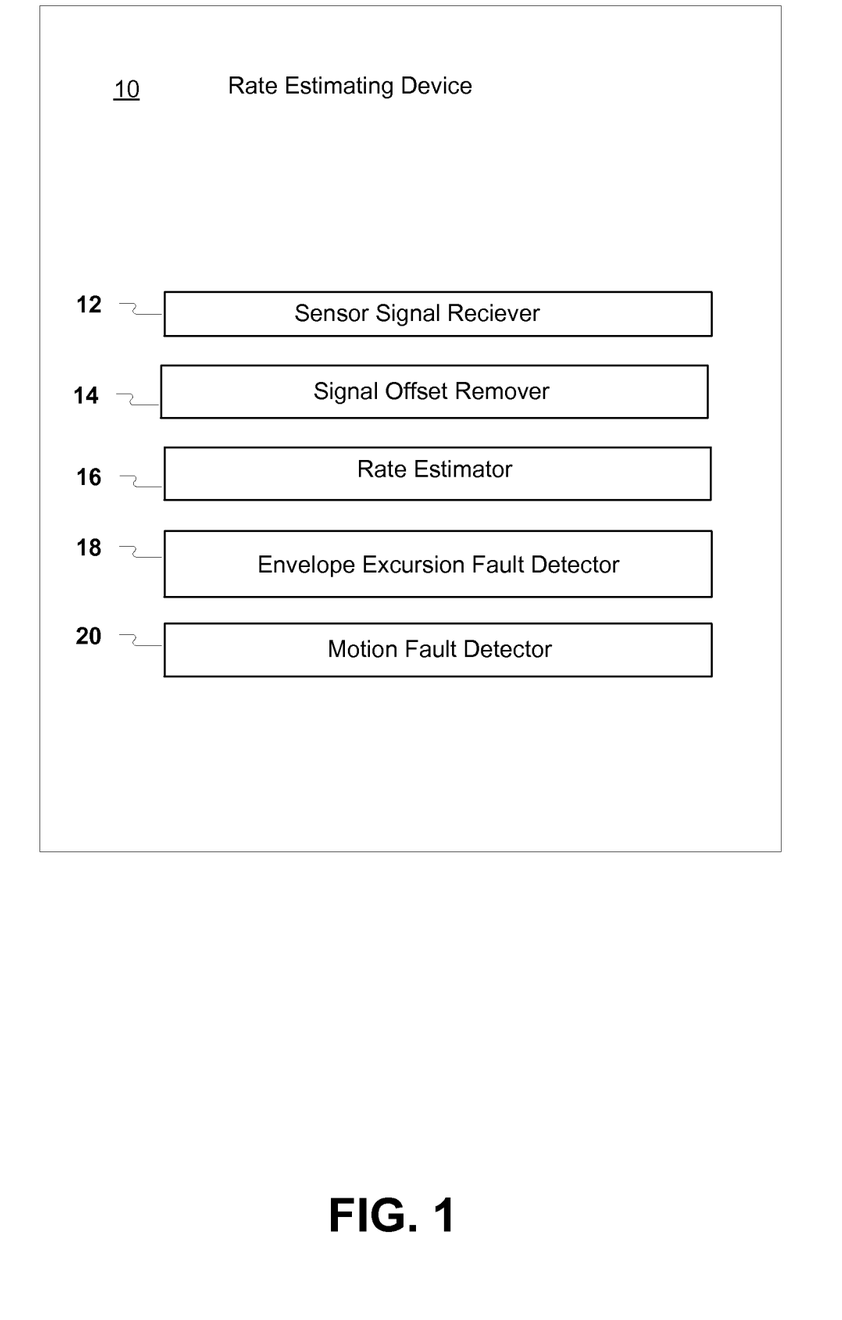
FIG. 1 illustrates a block diagram depicting an exemplary rate estimating device using the Hilbert transform in accordance with an embodiment.

FIG. 1 illustrates a block diagram depicting an exemplary rate estimating device using the Hilbert transform in accordance with an embodiment. An exemplary rate estimating device 10 employs a Hilbert transform process to continuously estimate biophysiological rates, for example, a heart rate. The rate estimating device 10 includes a sensor signal receiver 12, a signal offset remover 14, a rate estimator 16, an envelope excursion fault detector 18, and a motion fault detector 20. The rate estimating device 10 processes a stream of biophysiological sensor data over time and outputs a stream of biophysiological feature data, for example, an interbeat interval or instantaneous heart rate.

The sensor signal receiver 12 receives biophysiological sensor data as input, for example, a photoplethysmogram (PPG) sensor signal, and converts the data to an appropriate format for signal processing. In various embodiments, biophysiological sensor data that may be analyzed using the method described in this disclosure include, for example, optical sensor data (e.g., (PPG)), electrical potential sensor data (e.g., an electrocardiogram (ECG or EKG), and electrical impedance sensor data (e.g., Bio Z® impedance cardiography (ICG)).

The signal offset remover 14 removes a direct-current (DC) offset from the signal, such that the signal is centered at approximately zero volts. For example, the signal offset remover 14 implements a high-pass filter to remove the signal DC offset. The signal offset remover 14 provides initialization.

The rate estimator 16 implements additional bandpass filtering and applies Hilbert transform approximations to estimate the periodic rate of the signal. The Hilbert-transform based approach to rate estimation of a quasiperiodic signal constructs an analytic signal which has a real part as the original signal and an imaginary part that is phase-shifted from the original by 90 degrees. The phase shift may be accomplished either explicitly in the Fourier domain, or using a time-domain filter designed for the purpose. The phase of the analytic signal is differentiated to obtain an instantaneous frequency.

In order to facilitate relatively accurate frequency estimation using the Hilbert transfer that is relatively tolerant of DC-level shifts, the rate estimating device 10 simultaneously combines three basic approaches to mitigate these effects. The process implements phase-compensated infinite impulse response (IIR) digital filtering, motion masking to handle motion artifacts and activity corruption, and envelope masking based on Hilbert analytic amplitude to increase robustness with respect to rate changes.

The excursion fault detector 18 applies Hilbert envelope-based masking based on the Hilbert analytic amplitude to increase robustness with respect to rate changes. The motion fault detector 20 applies motion masking to handle motion artifacts and activity corruption.

The Hilbert-transform based approach has excellent signal recovery characteristics for stable, smooth signals, even when the instantaneous frequency changes over a small number of signal periods. The approach is also fairly robust with respect to uniform Gaussian noise, but is less tolerant of non-Gaussian noise. The approach is particularly affected when the fundamental frequency is corrupted by low frequency noise. Heuristically, the analytical signal is presumed to have a zero-mean, and therefore the low frequency content generally is ascribed to either changes in amplitude or changes in frequency/phase. Shifts in the mean amplitude, or DC level, may be especially problematic, since these may cause large deviations in the instantaneous frequency.

Sensor signal processing inference approaches that improve the robustness to DC-level shifts have a direct impact on the required mechanical interface between the body and the sensor. With regard to some wearable devices, this requirement translates into tightness of the attachment, which translates into comfort for many mechanical designs. As a result, increased system tolerance with regard to DC-level shifts may enable looser, more comfortable wearable device designs.

Figure 2:
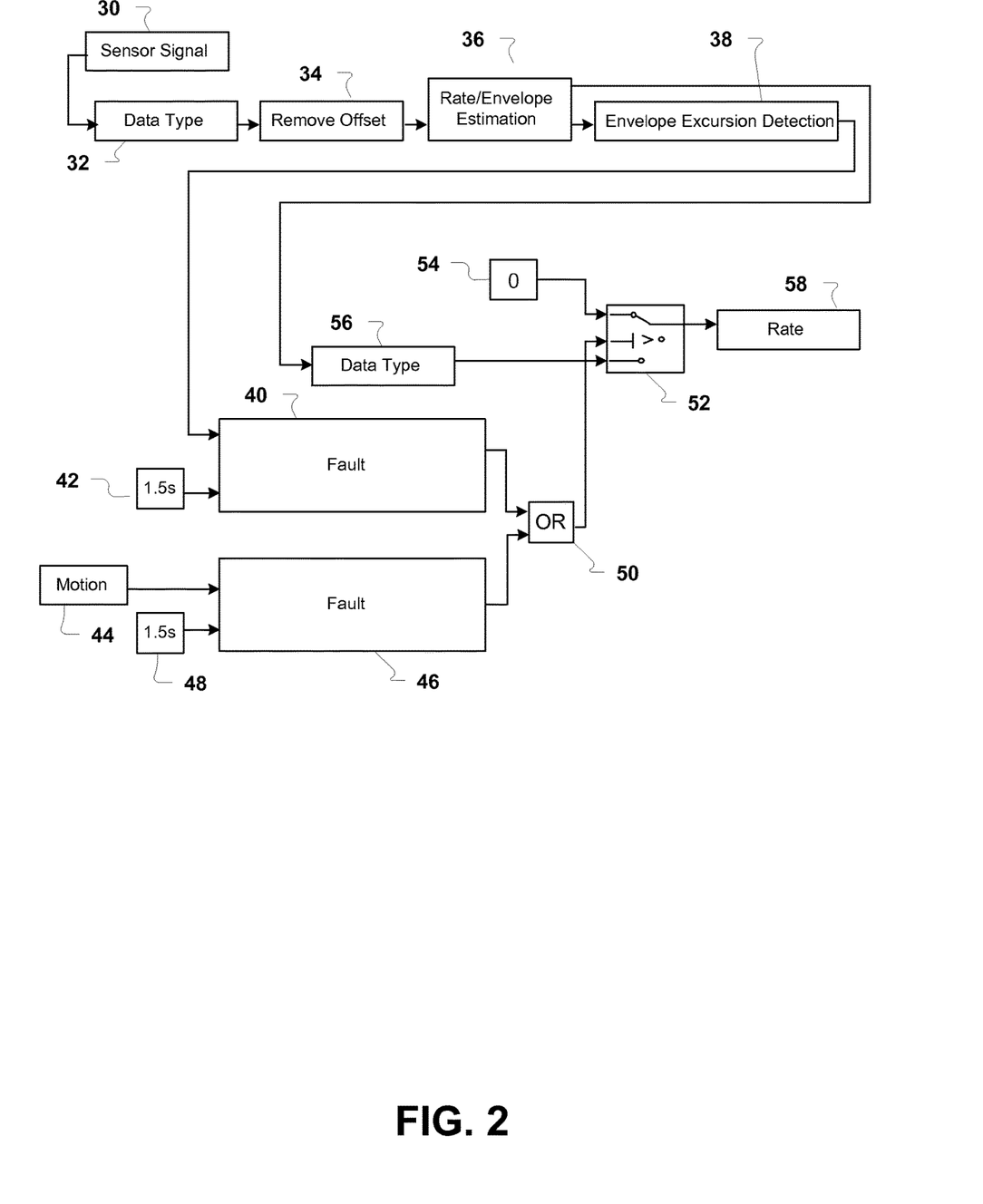
FIG. 2 illustrates a flowchart representing an exemplary method of estimating a biophysiological rate using the Hilbert transform in accordance with an embodiment.

FIG. 2 illustrates a flowchart representing an exemplary method of estimating a biophysiological rate using the Hilbert transform in accordance with an embodiment. A process of continuous estimation of biophysiological rates (e.g., a heart rate) based on the Hilbert transform may be performed, for example, by a biophysiological rate estimating device 10. The process performs rate estimation based on fluctuations in sampled raw data. The process begins by receiving biophysiological sensor data 30 as input, for example, an optical PPG sensor signal.

At 32, the digital data type of the sensor data 30 is converted, for example, to a double-precision floating-point number for further processing. At 34, when the sensor data includes an essentially direct-current (DC) component, a high-pass filter (HPF) removes the DC offset to produce an output signal that is centered approximately at zero volts. Additional bandpass filtering may be performed to accomplish signal smoothing and phase compensation, and Hilbert transform-based approximations may be applied to determine the frequency of the output signal of 34. At 36, the periodic rate associated with the output signal of 34 is estimated.

At 38, an envelope excursion detection, for example, based on Hilbert transform, is performed to detect an envelope excursion fault and set an envelope excursion fault detector flag. At 40, if an envelope excursion fault detector flag is received, a fault flag is set during an envelope excursion fault hysteresis time period 42 (e.g., 1.5 s).

At 46, if a motion signal 44 is received from a motion sensor, such as an onboard accelerometer in a wearable device, a fault flag is set and output during a motion fault hysteresis time period 48. For example, a flag is triggered by a fixed threshold with respect to the accelerometer signal. The input motion estimation method masks the heart rate signal during motions that may lead to undesirable DC shifts. Motion masking may reduce or eliminate the signal effects generated by subject movements, for example, that of a wearable sensor.

At 50, if a fault flag from either 40 or 46 is detected by the logical operator (e.g., "OR"), the switch at 52 produces an output based on the masked rate output (e.g., zero) 54. Otherwise, the estimated rate output of 36 is converted to an appropriate data type format at 56, and outputted at 52. The output rate of 52 is sent at 58.

Figure 3:
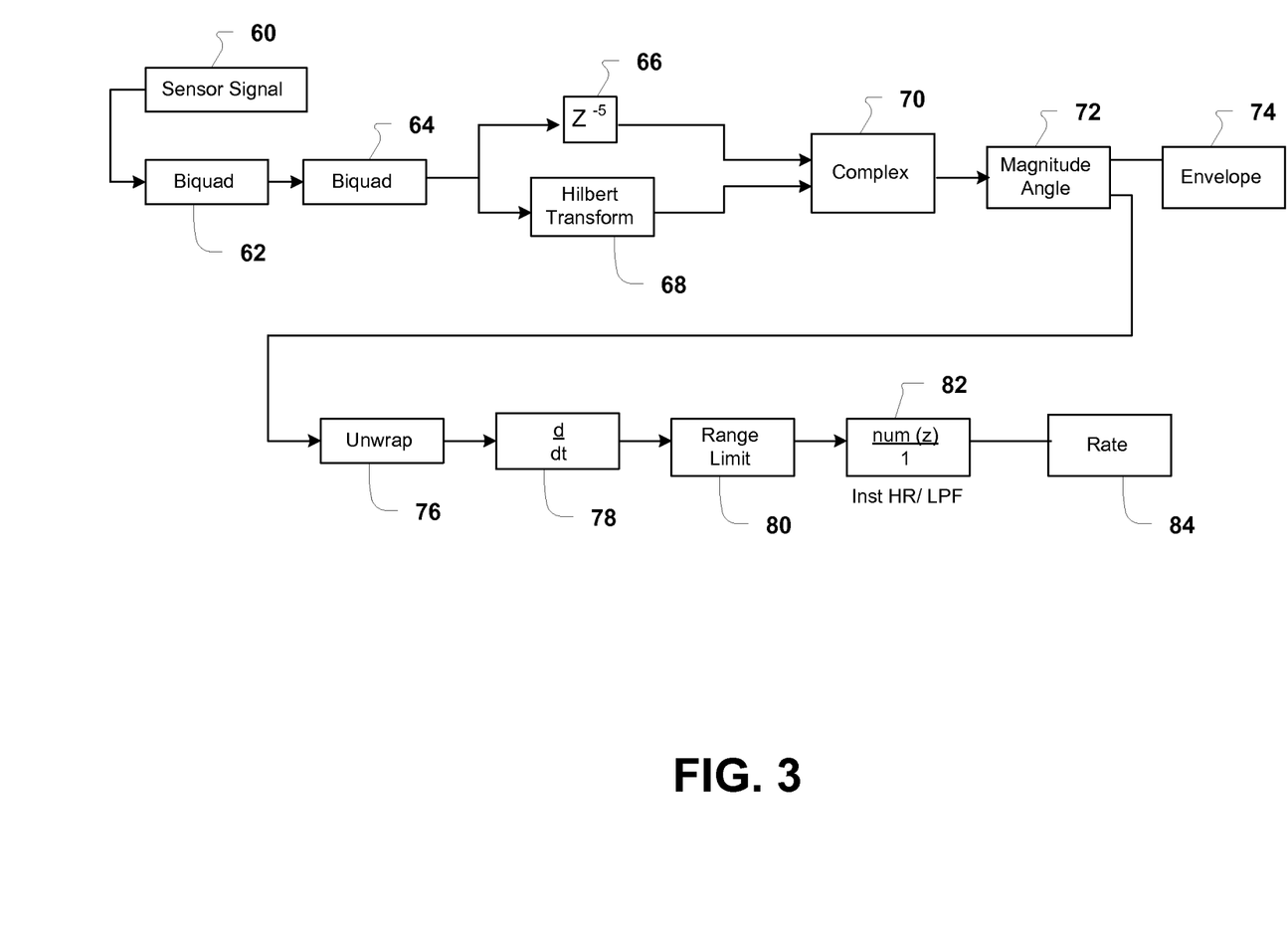
FIG. 3 illustrates a flowchart representing an exemplary method of sensor signal filtering and frequency estimation in accordance with an embodiment.

FIG. 3 illustrates a flowchart representing an exemplary method of sensor signal filtering and frequency estimation in accordance with an embodiment. FIG. 3 presents additional detail regarding the DC offset removal bandpass filtering and Hilbert-based frequency estimation performed at 36 of FIG. 2, according to one embodiment. The process begins by receiving a preprocessed sensor signal 60. At 62, a bandpass filter filters the preprocessed sensor signal 60 using a design for high-pass rejection to mask low-frequency noise, for example, a biquadratic filter having low and high filter cutoff frequencies of 30 and 150 beats per minute (bpm), respectively.

At 64, an all-pass phase compensation bandpass filter, for example, a phase-compensated infinite impulse response (IIR) biquadratic filter filters an output signal of 62. This approach permits the use of a lower-order filter than would be required, for example, using a linear-phase finite impulse response (FIR) filter. The lower-order filter may avoid lag issues and reduce the required microcontroller memory with respect to some FIR designs, which is particularly important in embedded platforms. Further, phase compensation may reduce or minimize corruption to the analytic signal used to estimate the output rate.

At 66, an integer delay (e.g., $Z^{-5}$) is applied to the output signal of 64. At 68, a Hilbert transform approximation is performed in parallel on the output signal of 64, for example, using the Filter Design and Analysis Tool (FDATool) function in MATLAB® high-level language and interactive environment by MathWorks®. The output signals of 66 and 68 make up the analytic signal components. At 70, the output signal of 66 is used as a real component for a complex number and the output signal of 68 is used as an imaginary component for the complex number. The complex number makes up an analytic signal. At 72, the analytic signal is converted to a data stream with magnitude-angle format. At 74, the magnitude, or absolute value, of the data stream is output as a signal envelope (e.g., PPG Env).

At 76, the phase angles of the data stream including the signal envelope are corrected to smooth the data stream and provide a corrected envelope signal, for example, using an unwrap function in MATLAB®. At 78, the discrete derivative of the corrected envelope signal with respect to time is calculated. At 80, upper and lower limits are imposed to limit the output signal of 78 to a predetermined range. For example, a saturation function in MATLAB® may be used to limit a signal range of the output signal of 78. At 82, a low-pass filter filters the output signal of 80 to smooth and provide an estimated rate 84.

Figure 4:
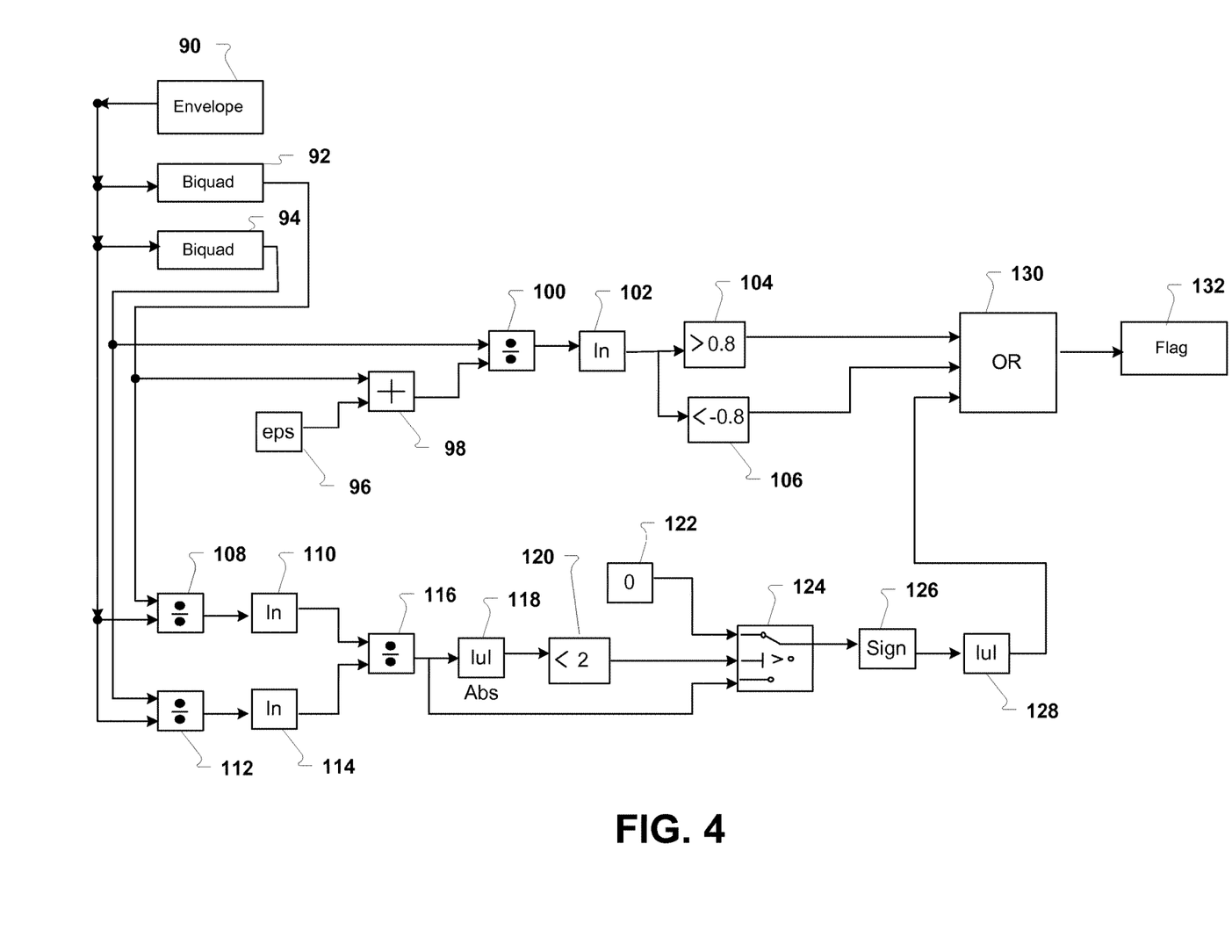
FIG. 4 illustrates a flowchart representing an exemplary method of sensor signal envelope excursion detection in accordance with an embodiment.

FIG. 4 illustrates a flowchart representing an exemplary method of sensor signal envelope excursion detection in accordance with an embodiment. FIG. 4 presents additional detail regarding the sensor signal envelope excursion detection performed at 38 of FIG. 2, according to one embodiment. The process begins at 90 by receiving the signal envelope (e.g., PPG Env) from block 74 of FIG. 3. At 92 and 94, low-pass filtering is performed in parallel on the signal envelope to produce relatively fast-varying and relatively slow-varying smoothed versions of the signal envelope. For example, a biquadratic low-pass filter having a cutoff frequency of approximately 0.5 Hz is applied on the signal envelope at 92, and a biquadratic low-pass filter having a cutoff frequency of approximately 0.067 Hz is applied in parallel on the signal envelope at 94.

At 98, a divide-by-zero offset 96 is added to the slow-varying version of the envelope signal from 92. At 100, the fast-varying version of the envelope signal from 94 is divided by the output signal of 98. At 102, the natural log of output signal of 100 is evaluated. At 104, if the output signal of 102 is compared to and greater than a predetermined constant (e.g., 0.8), the logical outcome of the comparison is "true." At 106, if the output signal of 102 is compared to and less than a predetermined constant (e.g., −0.8), the logical outcome of the comparison is "true."

At 108, the slow-varying version of the envelope signal from 92 is divided by the envelope signal from 90. At 110, the natural log of the output signal of 108 is evaluated. At 112, the fast-varying version of the envelope signal from 94 is divided by the envelope signal from 90. At 114, the natural log of the output signal of 112 is evaluated. At 116, the output signal of 110 is divided by the output signal of 112. At 118, an absolute value for the output signal of 116 is determined.

At 120, if the absolute value is compared to and less than a predetermined constant (e.g., 2), the logical outcome of the comparison is "true,". At 124, a default output (e.g., zero) 122 is selected if the logical outcome of 120 is "true", otherwise, the output signal of 116 is selected. At 126, if the output value of 124 is zero, the result is also zero. However, at 126, if the output value of 124 is greater than or less than zero, the result is one (1) or negative one (−1), respectively. At 128, an absolute value of the result of 126 is taken. At 130, if a logical "true," or "1," is detected at the logical operator (e.g., "OR"), then an envelope excursion fault detector flag is output at 132.

The Hilbert transform envelope-based masking is used to detect relatively high variability and remove associated data points from the output rate estimate. Since the frequency estimation approach is known to work well for relatively consistent quasiperiodic signals, excessive variability in the analytic amplitude is a reliable indicator of errors in the frequency estimation.

Using the method of FIG. 4, deviations are detected between the analytic signal amplitude and each relatively slow-varying and fast-varying smoothed versions of the signal. Significant deviations indicate non-stationary behavior that is likely to lead to corrupted rate estimates. The deviations are compared to preset limits and a flag is set if the deviations are above a threshold.

The deviation detection method of FIG. 4 essentially detects deviations in the log-ratio of the signal. The Hilbert envelope is typically consistent, but is sensitive to transient irregularity in the sensor signal. These conditions, essentially deviations in the signal log ratio, function as a "burstiness" detector to the Hilbert envelope, detecting irregularities between the Hilbert envelope and relatively slow and fast smoothed versions of the signal.

Figure 5:
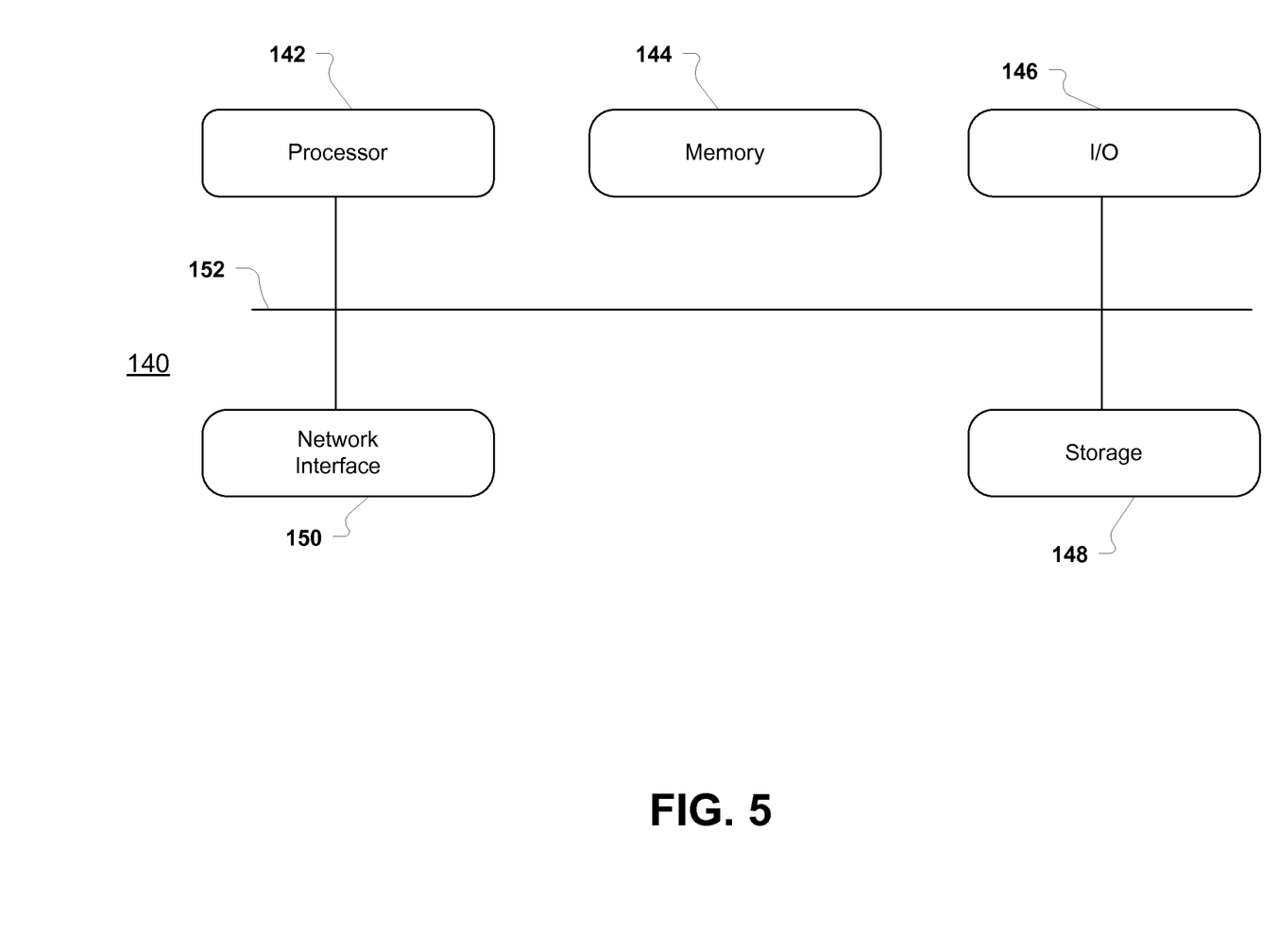
FIG. 5 illustrates a schematic view depicting an exemplary general computing system that may implement a rate estimating device in accordance with an embodiment.

FIG. 5 illustrates a schematic view depicting an exemplary general computing system that may implement a rate estimating device in accordance with an embodiment. An exemplary computing device 140 that may implement a rate estimating device includes a processor 142, a memory 144, an input/output device (I/O) 146 storage 148 and a network interface 150. The various components of the computing device 140 are coupled by a local data link 152, which in various embodiments incorporates, for example, an address bus, a data bus, a serial bus, a parallel bus, or any combination of these.

The computing device 140 may be used, for example, to implement the present method of estimating biophysiological rates. Programming code, such as source code, object code or executable code, stored on a computer-readable medium, such as the storage 148 or a peripheral storage component coupled to the computing device 140, may be loaded into the memory 144 and executed by the processor 142 in order to perform the present method of estimating biophysiological rates.

Aspects of this disclosure are described herein with reference to flowchart illustrations or block diagrams, in which each block or any combination of blocks may be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a computer-readable medium having computer-readable program code embodied thereon.

It will be understood that various modifications may be made. For example, useful results still could be achieved if steps of the disclosed techniques were performed in a different order, and/or if components in the disclosed systems were combined in a different manner and/or replaced or supplemented by other components. Accordingly, other implementations are within the scope of the following claims.

What is claimed is:

1. An apparatus for determining a biophysiological feature, the apparatus comprising:
   a memory having machine instructions stored therein;
   a processor coupled to the memory;
   a biophysiological sensor coupled to the processor, the biophysiological sensor configured for application to a patient and operable for detecting signals in the patient associated with measuring a quasiperiodic function; and
   an input/output device;
   wherein the processor executes the machine instructions to:
      receive a quasiperiodic data stream for the measured quasiperiodic function from the biophysiological sensor, remove at least a portion of an offset from the quasiperiodic data stream to provide a smoothed data stream by filtering the quasiperiodic data stream through a bandpass filter and phase compensating the filtered quasiperiodic data stream, transform the smoothed data stream into an analytic data stream using a Hilbert transform approximation, calculate a time derivative associated with a phase angle of the analytic data stream, provide, to a user via the input/output device, an output data stream derived from a frequency, wherein the frequency is the time derivative of the quasiperiodic data stream and wherein the output data stream comprises the biophysiological feature, and mask the output data stream while a sensor motion fault is detected.

2. The apparatus of claim 1, wherein the processor further executes the machine instructions to:

determine a magnitude of the analytic data stream, the magnitude comprising an envelope of the quasiperiodic data stream, and detect a transient irregularity of the analytic data stream based on the envelope.

3. The apparatus of claim 2, wherein the processor further executes the machine instructions to detect the transient irregularity of the analytic data stream based on:

smoothing the envelope through a first filter with a first cutoff frequency, the output of the first filter comprising a first smoothed envelope, smoothing the envelope through a second filter with a second cutoff frequency that is lower than the first cutoff frequency, the output of the second filter comprising a second smoothed envelope, comparing a first logarithmic ratio of the envelope and the first smoothed envelope with a second logarithmic ratio of the envelope and the second smoothed envelope, and masking the output data stream while the comparison exceeds a predetermined limit.

4. The apparatus of claim 1, wherein the quasiperiodic data stream is an electrocardiogram (ECG) electrode signal.

5. The apparatus of claim 1, wherein the quasiperiodic data stream is a photoplethysmogram (PPG) sensor signal.

6. The apparatus of claim 1, wherein the quasiperiodic function is a sensed heartbeat and the biophysiological feature is a heartbeat rate.

7. The apparatus of claim 1, wherein the quasiperiodic function is a sensed heartbeat and the biophysiological feature is a heart interbeat interval.

8. A method for determining a biophysiological feature, the method comprising:

measuring a quasiperiodic function with a biophysiological sensor that is configured for application to a patient and operable for detecting signals in the patient associated with the quasiperiodic function;

receiving, at a sensor signal receiver, a quasiperiodic data stream for the measured quasiperiodic function from the biophysiological sensor;

removing, with a processor comprising a signal offset remover coupled to the sensor signal receiver and comprising a bandpass filter, at least a portion of an offset from the quasiperiodic data stream to provide a smoothed data stream by filtering the quasiperiodic data stream through the bandpass filter and phase compensating the filtered quasiperiodic data stream;

with a rate estimator of the processor coupled to the signal offset remover: transforming the smoothed data stream into an analytic data stream using a Hilbert transform approximation; calculating a time derivative associated with a phase angle of the analytic data stream; and providing, to a user via an input/output device, an output data stream derived from a frequency, wherein the frequency is the time derivative of the quasiperiodic data stream and wherein the output data stream comprises the biophysiological feature; and masking, with an excursion fault detector coupled to the rate estimator, the output data stream while a sensor motion fault is detected.

9. The method of claim 8, further comprising and with the rate estimator:

determining a magnitude of the analytic data stream, wherein the magnitude is an envelope of the quasiperiodic data stream; and detecting a transient irregularity of the analytic data stream based on the envelope.

10. The method of claim 9, wherein said detecting the transient irregularity of the analytic data stream based on the envelope comprises:

smoothing the envelope through a first filter with a first cutoff frequency, wherein the output of the first filter is a first smoothed envelope;

smoothing the envelope through a second filter with a second cutoff frequency that is lower than the first cutoff frequency, wherein the output of the second filter is a second smoothed envelope;

comparing a first logarithmic ratio of the envelope and the first smoothed envelope with a second logarithmic ratio of the envelope and the second smoothed envelope; and masking the output data stream while the comparison exceeds a predetermined limit.

11. The method of claim 8, wherein the quasiperiodic data stream is an electrocardiogram (ECG) electrode signal.

12. The method of claim 8, wherein the quasiperiodic data stream is a photoplethysmogram (PPG) sensor signal.

13. The method of claim 8, wherein the quasiperiodic function is a sensed heartbeat and the output data stream is selected from the group consisting of: a heartbeat rate; and a heart interbeat interval.

14. An apparatus for signal processing, the apparatus comprising:

a memory having machine instructions stored therein;

a processor coupled to the memory; and a biophysiological sensor coupled to the processor and operable for sensing a heartbeat of a patient;

wherein the processor executes the machine instructions to:

receive a signal comprising a quasiperiodic data stream for the sensed heartbeat from the biophysiological sensor, remove at least a portion of an offset from the signal to center the signal at a target voltage and provide a smoothed data stream by filtering the signal through a bandpass filter and phase compensating the filtered quasiperiodic data stream, transform the smoothed data stream into an analytic data stream using a Hilbert transform approximation, calculate a time derivative associated with a phase angle of the analytic data stream, provide, to a user via an input/output device, an output data stream derived from a frequency, wherein the frequency is the time derivative of the quasiperiodic data stream and wherein the output data stream comprises at least one of a heartbeat rate and a heart interbeat interval, and mask the output data stream during a sensor motion fault.

15. The apparatus of claim 14, wherein the processor further executes the machine instructions to:

determine a magnitude of the analytic data stream, the magnitude comprising an envelope of the quasiperiodic data stream, and detect a transient irregularity of the analytic data stream based on the envelope.

16. The apparatus of claim 15, wherein the processor further executes the machine instructions to detect the transient irregularity of the analytic data stream based on:

smoothing the envelope through a first filter with a first cutoff frequency, the output of the first filter comprising a first smoothed envelope, smoothing the envelope through a second filter with a second cutoff frequency that is lower than the first cutoff frequency, the output of the second filter comprising a second smoothed envelope, comparing a first logarithmic ratio of the envelope and the first smoothed envelope with a second logarithmic ratio of the envelope and the second smoothed envelope, and masking the output data stream while the comparison exceeds a predetermined limit.

17. The apparatus of claim 14, wherein the quasiperiodic data stream is an electrocardiogram (ECG) electrode signal.

18. The apparatus of claim 14, wherein the quasiperiodic data stream is a photoplethysmogram (PPG) sensor signal.

19. The apparatus of claim 14, wherein the biophysiological sensor is configured for application to the patient and is operable for detecting signals in the patient associated with the heartbeat.

* * * * *